United States Patent
Ekanayake

(10) Patent No.: US 6,632,804 B2
(45) Date of Patent: Oct. 14, 2003

(54) COMPOSITIONS USEFUL IN THE TREATMENT OF DISEASES OF CONNECTIVE TISSUES

(75) Inventor: V. G. Sunetra Ekanayake, Halifax (CA)

(73) Assignee: Ocean Nutrition Canada Limited, Nova Scotia (CA)

( * ) Notice: Subject to any disclaimer, the term of this patent is extended or adjusted under 35 U.S.C. 154(b) by 62 days.

(21) Appl. No.: 09/842,742

(22) Filed: Apr. 25, 2001

(65) Prior Publication Data

US 2001/0044425 A1 Nov. 22, 2001

Related U.S. Application Data

(60) Provisional application No. 60/200,361, filed on Apr. 28, 2000.

(51) Int. Cl.$^7$ .............................. A01N 43/04
(52) U.S. Cl. ............................................ 514/62
(58) Field of Search ................... 514/474, 62, 825; 424/648

(56) References Cited

U.S. PATENT DOCUMENTS

| | | | |
|---|---|---|---|
| 2,822,317 A | * 2/1958 | Gulesich et al. | 424/648 |
| 3,683,076 A | 8/1972 | Rovati | 514/62 |
| 4,745,129 A | * 5/1988 | Ikari et al. | 514/502 |
| 5,364,845 A | 11/1994 | Henderson | 514/54 |
| 5,405,613 A | * 4/1995 | Rowland | 424/439 |
| 5,587,363 A | 12/1996 | Henderson | 514/54 |
| 5,759,586 A | 6/1998 | Fuchs et al. | 424/686 |
| 6,177,476 B1 | * 1/2001 | Peterson et al. | 514/722 |
| 6,245,360 B1 | * 6/2001 | Markowitz | 424/641 |

FOREIGN PATENT DOCUMENTS

| | | | |
|---|---|---|---|
| EP | 25721 | 3/1981 | A61K/33/26 |
| GB | 2317109 | 3/1998 | A61K/33/30 |
| WO | WO98/16218 | 4/1998 | |

OTHER PUBLICATIONS

Barclay, et al, "Glucosamine", *The Annals of Pharmacotherapy* ( May, 1998) 32:574–79.
The Arthritis Society website, (http://www.arthritis.ca), Feb. 4, 2000, published by The Arthritis Society.
Linsenmayer, T.F., "Collagen", Chapter 1 in *Cell Biology of Extracellular Matrix, Second Edition*, Hay, Elizabeth D., ed., Plenum Press, NY (1991) pp. 7–13.
Maini, et al, "Aetiopathogenesis of Rheumatoid Arthritis" in *Mechanisms of Modes and Rheumatoid Arthritis*, Academic Press Ltd (1995) pp. 25–46.
Rashad et al, "Effect of Non–steroidal Anti–inflammatory Drugs on the Course of Osteoarthritis", *The Lancet* (Sep. 2, 1989) 2:519–521.
Herman et al, "The In Vitro Effect of Select Classes of Nonsteroidal Antiinflammatory Drugs on Normal Cartilage Metabolism", *The Journal of Rheumatology* (1986) 13(6):1014–1018.
Levenson G.E., "The Effect of Ascorbic Acid on Monolayer Cultures of Three Types of Chondrocytes", *Experimental Cell Research* (1969) 55:225–228.
Deal and Moskowitz, PubMed Abstract PMID 10356424 for "Neutraceuticals as therapeutic agents in osteoarthritis. The role of glucosamine, chondroitin sulfate, and collagen hydrosylate", *Rheum. Dis. Clin. North Am.* (May, 1999) 25(2):379–95.
Sandy et al, "Chondrocyte–mediated catabolism of aggrecan: aggrecanase–dependent cleavage induced by interleukin-1 or retinoic acid can be inhibited by glucosamine", *Biochem J.* (1998) 335:59–66.
Ekanayake S and B.K. Hall, "Hypertrophy is not a prerequisite for type X collagen expression or mineralization of chondrocytes derived from cultured chick mandibular ectomesenchyme", *Int. J. Dev. Biol.* (1994) 38:683–694.
Tropicana orange juice product information and label information—Internet extract May 15, 2001.
Minute Maid orange juice product information and label information—Internet extract May 15, 2001.
Nath, M. et al. Treatment of anaemia of rheumatoid arthritis with oral iron and vitamin C. Clinician, vol. 38, No. 8, 1974, pp. 334–340.
K.B. Raja E.A.. In vitro duodenal iron uptake and serum and mucosal iron protein levels, with special reference to rheumatoid arthritis. British Journal of Rheumatology, vol. 34, No. 11, 1995, pp. 1041–1047, XP001064442, p. 1041.
Dialog Abstract of DE 20004010 UL, Mar. 2, 2000, Febena Pharma GMBH.

* cited by examiner

Primary Examiner—Kathleen K. Fonda
(74) *Attorney, Agent, or Firm*—Welsh & Katz, Ltd.

(57) ABSTRACT

Compositions comprising ferrous ion and an ascorbate have a synergistic effect on cartilage development. Therapeutic compositions comprising ferrous ion and an ascorbate are therefore useful in the treatment of osteoarthritis. The addition of a glucosamine, such as glucosamine hydrochloride, to the composition has a further enhanced effect on cartilage production. Therapeutic compositions comprising ferrous ion, an ascorbate and a glucosamine derivative are even more useful in the treatment of osteoarthritis.

28 Claims, 6 Drawing Sheets

CONTROL

RA ONLY

RA + ONC 114

RA + OSTEO BI-FLEX

RA + SCHIFF

COMPOSITIONS USEFUL IN THE TREATMENT OF DISEASES OF CONNECTIVE TISSUES

This application claims the benefit of U.S. Provisional Application No. 60/200,361, filed Apr. 28, 2000, which provisional application is hereby incorporated by reference to the extent that it is compatible with this application.

FIELD OF THE INVENTION

This invention relates to therapeutic compositions for use in treating diseases of connective tissues in animals, more particularly, for use in treating osteoarthritis in mammals, such as humans, dogs, cats, pigs, horses, cows, goats and sheep.

BACKGROUND OF THE INVENTION

Arthritic diseases, characterized by the pain, inflammation and stiffness of the joints leading to reduced range of mobility, are due to the degradation of connective tissue (mainly cartilage) in joints. Such diseases particularly affect weight-bearing joints such as the hips, knees, spine, ankles and feet and those joints with frequent movement such as hands, arms and neck.

Osteoarthritis (OA) in particular is a degenerative disease of the joint cartilage resulting in narrowing of the joint space and changes in the underlying bone (Barclay, et al., *The Annals of Pharmacotherapy*, (May, 1998) 32: 574–79). OA is the most common form of arthritis among people and it affects approximately one in ten people in North America. People of all ages can get OA, but it more often affects older people and women. For example, 85% of the age group 70 years or older is affected by OA (The Arthritis Society website, (http://www.arthritis.ca), Feb. 4, 2000, published by The Arthritis Society). OA is not limited to humans, but occurs in other mammals such as horses, dogs, cats, mice and guinea pigs as well, making OA one of the most common sources of chronic pain seen by veterinarians.

The cause of OA could be one or more of the following: nutritional deficiencies, aging, long-term stress on joints (e.g. athletes, manual workers), old joint injuries and genetic factors. The tissue that is directly affected is the cartilage covering the end of long bones in joints that provide cushioning for the bones during movements. In normal cartilage, chondrocytes (cartilage cells) maintain a balance between the synthesis and degradation of cartilage matrix. However, when the degradation of cartilage matrix exceeds that of synthesis, it leads to OA. When the disease progresses further, bone underlying the articular cartilage in joints becomes exposed in certain places. In addition, irregular bone growth occurs in the place of degenerating cartilage resulting in rough bony alterations. As a result, the joint loses its smooth functioning leading to joint pain, stiffness and swelling thus limiting mobility.

Cartilage is a unique tissue having cells (chondrocytes) embedded in their own secretions which forms the cartilage matrix. The cartilage matrix is composed of a meshwork of collagen fibrils and proteoglycan aggregates filling the space between collagen. Collagen fibrils provide high tensile strength and proteoglycan aggregates provide internal swelling pressure due to their hydrophilic nature. Cartilage cells are remarkable in that they have the ability to proliferate while synthesizing and remodeling the matrix around them. These two features provide the cartilage the ability to repair itself during damage and replenish wear and tear.

Collagen fibrils are a major component of the cartilage matrix. Collagen is made from amino acids, particularly lysine, proline and glycine. Fibrillar collagens are triple helical molecules. The three α-chains of each collagen molecule are initially produced as individual peptides which are further processed by the hydroxylation of proline and lysine residues bound to the peptides. The hydroxyproline and hydroxylysine so produced facilitate hydrogen bonding between the three α-chains, this being essential for the formation of the triple helical structure (Linsenmayer, *Collagen*, Chapter 1 in *Cell Biology of Extracellular Matrix, Second Edition*, Elizabeth D. Hay, ed., Plenum Press, N.Y. (1991) pp. 7–13). Unlike individual collagen peptides (α-chains) that become easily digested by proteolytic enzymes, triple helical collagen is extremely stable to proteolytic enzymes, heat and variations of pH. Therefore, the most important step in collagen synthesis is the formation of the triple helical structure by hydroxylation of amino acids in collagen α-chains. While the Linsenmayer reference suggests that ascorbic acid and ferrous ions are cofactors in the hydroxylation of proline and lysine to hydroxyproline and hydroxylysine respectively, Linsenmayer does not suggest that a therapeutic composition comprising ascorbic acid and ferrous ions would be useful in the treatment of osteoarthritis.

Proteoglycan aggregates are the other major component of the cartilage matrix. Cartilage proteoglycans are macromolecules comprised of glycosaminoglycan (GAG) chains, such as chondroitin sulphate and keratan sulphate, that are made up of repeating disaccharide units containing aminosugars, attached to a core protein. Proteoglycans are in turn attached to a backbone of hyaluronic acid, which is yet another GAG. Among GAGs of cartilage, hyaluronic acid is unique in that it is an extremely large molecule with about 25,000 repeating disaccharide units (in comparison, chondroitin sulphate and keratan sulphate have only about 250 and 80 repeating disaccharide units respectively). About 50% of hyaluronic acid and keratan sulphate are glucosamine.

Rheumatoid arthritis (RA) is a disease that has some similar symptoms to osteoarthritis, but whose cause is considerably different. RA is known to be an autoimmune disease (Maini, et al., *Aetiopathogenesis of Rheumatoid Arthritis*. in *Mechanisms and Modes of Rheumatoid Arthritis*, (1995) Academic Press Ltd. pp. 25–46), in which the immune system attacks body tissues as if they were foreign invaders, culminating in inflammatory and destructive responses in joints as well as other tissues. Although the exact cause of RA is not completely understood, contributing factors are believed to include food allergies, pathogens, leaky gut syndrome and hereditary factors. Because of the difference in cause of RA as opposed to diseases of the connective tissues such as osteoarthritis, it is not necessarily expected that treatment for RA would be effective against osteoarthritis and the like.

A number of treatments for osteoarthritis and like diseases are commonly used. Most of the treatments currently available are aimed towards reducing symptoms but do not deal with the underlying tissue degradation. The use of steroids, corticosteroids and other anti-inflammatory agents, such as non-steroidal anti-inflammatory drugs (NSAIDs), for example, aspirin™, relieve symptoms and reduce pain but also do not deal with the underlying tissue degeneration. NSAIDs may even speed up the progression of OA (Rashad et al., *The Lancet*, (September, 1989) 2: 519–521, and, Herman et al., *The Journal of Rheumatology*, (1986) 13: 1014–1018).

Therapies based on the regeneration of connective tissue, particularly cartilage, are attractive long-term solutions to the problem of osteoarthritis. To this end, there have been a number of disclosures of therapeutic compositions for the treatment of arthritic diseases.

U.S. Pat. Ser. No. 3,683,076 issued on Aug. 8, 1972 to Rovati discloses pharmaceutical compositions comprising the glucosamine salts—glucosamine sulphate and glucosamine hydroiodide—for the treatment of osteoarthritis and rheumatoid arthritis.

U.S. Pat. Ser. No. 5,587,363 issued on Dec. 24, 1996 to Henderson discloses therapeutic compositions comprising a synergistic combination of certain aminosugars (glucosamine and its salts) with GAG's (chondroitin and its salts) for the repair and replacement of connective tissue. Henderson suggests that Zn, Mn and Vitamin C play a role in the synthesis of procollagen which is a building block of collagen and that Cu, Fe and Vitamin C play a role in the synthesis of collagen from procollagen. However, Henderson does not disclose synergistic compositions of ferrous ion and an ascorbate. Henderson further suggests that glucosamine is a building block in the synthesis of procollagen and that procollagen is a building block in proteoglycan synthesis. However, it is generally accepted that glucosamine is not a building block of procollagen, but is a building block of proteoglycan, while amino acids are the building blocks of procollagen which becomes further processed to give rise to collagen.

Great Britain application Serial Number 2,317,109 published on Mar. 16, 1998 discloses a therapeutic composition for the treatment and repair of connective tissue in mammals comprising glucosamine, chondroitin sulphate and one or both of ascorbic acid and zinc sulphate. This application teaches that ascorbic acid and zinc sulphate serve as catalysts in the metabolic pathways whereby cartilage and related tissues are produced from the chondroitin sulphate and glucosamine building blocks. It further teaches that one of ascorbic acid and zinc sulphate may be omitted from the composition. This application does not teach a role for ascorbic acid and ferrous ion in the production of collagen nor does it teach a synergistic combination of ferrous ion and ascorbic acid in the production of connective tissue.

Barclay (Barclay, et al., *The Annals of Pharmacotherapy*, (May, 1998) 32: 574–79) teaches the use of glucosamine derivatives, such as the sulphate, hydrochloride and chlorhydrate salts as well as N-acetylglucosamine, for the treatment of osteoarthritis. Barclay suggests that glucosamine can be used in combination with herbs, vitamins and minerals including the salts of magnesium, potassium, copper, zinc and selenium and vitamins A and C. There is no disclosure of a therapeutic combination of ferrous ion and ascorbic acid.

Levenson (Levenson, G. E., *Experimental Cell Research*, (1969) 55: 225–228) teaches the effect of ascorbic acid on chondrocytes. Levenson suggests that ascorbic acid plays a role in the production of cartilaginous material but does not disclose a combination of ascorbic acid and ferrous ion.

Deal (Deal and Moskowitz, *Rheum. Dis. Clin. North. Am.*, (May, 1999) 25(2): 379–95) discloses nutraceuticals as therapeutic agents in osteoarthritis comprising glucosamine and chondroitin sulphate. Glucosamine derivatives have been shown to be as effective as NSAIDs in relieving the symptoms of OA without having the adverse side effects of NSAIDs.

Sandy (Sandy, et al., *Biochem. J.*, (1998) 335: 59–66) discloses the inhibitory effect of glucosamine on aggrecanase, an enzyme that breaks down aggrecan in cartilage. Test formulations also contain ascorbic acid but there is no discussion of its role. Sandy does not teach the combination of ferrous ion and ascorbic acid in a therapeutic composition for the treatment of osteoarthritis.

European Patent Serial Number 25,721 published on Mar. 25, 1981 discloses an oral medication for the treatment of rheumatoid arthritis comprising a mixture of a variety of metals including ferrous ions in the form of ferrous sulphate. There is no discussion of the role of ferrous ions, nor is there any suggestion that ascorbic acid may be used in combination, nor is there any indication that the medication is effective against diseases of the connective tissue such as osteoarthritis. As has been discussed previously, rheumatoid arthritis is a different disease and it is not necessarily expected that medications useful against rheumatoid arthritis would be effective against diseases like osteoarthritis.

While the aforementioned compositions have been successful to varying degrees, none have proven to be entirely satisfactory in the treatment of diseases of the connective tissue like osteoarthritis. In particular, there is still a need for therapeutic compositions that further facilitate the production of collagen alone or in combination with the production of GAGs.

The disclosures of all previously mentioned patents, patent applications and non-patent references are hereby incorporated by reference to the extent that they are compatible with this application.

SUMMARY OF THE INVENTION

It is therefore an object of this invention to provide compositions and methods useful in treating a disease of connective tissue, particularly osteoarthritis, in animals, preferably mammals, more preferably humans, dogs, cats, pigs, horses, cows, goats and sheep.

It has now been found that a combination of ferrous ion and an ascorbate is surprisingly effective at facilitating the production of connective tissue and is thus useful in treating diseases of connective tissue. It has also been found that a glucosamine derivative in combination with ferrous ion and an ascorbate is even more surprisingly effective.

In accordance with the teachings of the present invention, there is provided a composition for treating a disease of connective tissue comprising a therapeutically effective amount of ferrous ion and a therapeutically effective amount of an ascorbate.

There is also provided a composition for treating a disease of connective tissue comprising a therapeutically effective amount of ferrous ion, a therapeutically effective amount of an ascorbate and a therapeutically effective amount of a glucosamine derivative.

There is still further provided a use of a composition comprising a therapeutically effective amount of ferrous ion and a therapeutically effective amount of an ascorbate for treating a disease of connective tissue. The use of ferrous ion and ascorbate may be in combination with a therapeutically effective amount of a glucosamine derivative.

There is still further provided a use of a therapeutically effective amount of ferrous ion and a therapeutically effective amount of an ascorbate for preparing a medicament for treating a disease of connective tissue. The use of ferrous ion and ascorbate may be in combination with a therapeutically effective amount of a glucosamine derivative.

There is yet still further provided a method of treating a disease of connective tissue comprising administering to a patient suffering from the disease, a composition comprising a therapeutically effective amount of ferrous ion and a therapeutically effective amount of an ascorbate. The administration of ferrous ion and ascorbate may also be in combination with the administration of a therapeutically effective amount of a glucosamine derivative.

DESCRIPTION OF PREFERRED EMBODIMENTS

The compositions of the present invention comprise ferrous ion and an ascorbate which, surprisingly, act synergistically in the development of cartilage. Without being limited to any particular mode of action, it is thought that the ferrous ion and the ascorbate influence the production of collagen.

While it is thought that ascorbate and ferrous ion enhance cartilage development by enhancing collagen synthesis, it is thought that glucosamine is a building block for glycosaminoglycans of proteoglycans in the cartilage matrix. The presence of the two types of cartilage enhancing agents further enhances total cartilage development. The addition of a glucosamine derivative to the ferrous ion/ascorbate composition provides a further enhanced effect on activity.

The term "treating" is used in a broad sense to encompass the amelioration of both the cause and the symptoms of a preexisting disease or condition, and the prevention or prophylaxis of the disease or condition.

Ferrous ions are preferably provided in the form of an inorganic or organic acid salt wherein the ferrous ion is accompanied by a counter-ion to balance the charge. Examples of inorganic counter-ions are sulphate, phosphate, nitrate, carbonate and halide. A preferred inorganic counter-ion is sulphate. Ferrous sulphate is a preferred inorganic form for ferrous ion. Examples of organic counter-ions are fumarate, gluconate, ascorbate, tartarate, succinate, lactate, citrate and maleate. Three preferred organic counter-ions are fumarate, ascorbate and gluconate. Ferrous fumarate, ferrous ascorbate and ferrous gluconate are three preferred organic forms for ferrous ion. Ferrous ascorbate has the advantage of providing both ferrous ion and ascorbate in the same compound.

Ferrous ion is present in the composition in an amount effective for promoting the development of connective tissue in the body. The actual amount is not critical provided it is sufficient to promote such development. The daily dosage of ferrous ion is preferably in the range of about 0.5 mg to about 200 mg, more preferably in the range of about 2 mg to about 200 mg, yet more preferably in the range of about 10 mg to about 18 mg, and most preferably is about 15 mg.

An ascorbate is any species capable of providing the ascorbate ion. Examples include ascorbic acid (Vitamin C) and salts of ascorbic acid including the potassium, sodium, calcium, ferrous and manganese salt. Ascorbic acid, calcium ascorbate and ferrous ascorbate are preferred. Ascorbic acid is the more preferred ascorbate.

Ascorbate is present in the composition in an amount effective for promoting the development of connective tissue in the body. The actual amount is not critical provided it is sufficient to promote such development. The daily dosage is preferably in the range of about 40 mg to about 1000 mg, more preferably in the range of about 40 mg to about 500 mg or about 100 mg to about 1000 mg, and most preferably is about 100 mg.

Glucosamine is an aminosugar. Examples of glucosamine derivatives are glucosamine itself, glucosamine hydrochloride, glucosamine hydroiodide, glucosamine chlorhydrate, glucosamine sulphate and N-acetyl glucosamine. Glucosamine hydrochloride and glucosamine sulphate are preferred glucosamine derivatives.

The glucosamine derivative is present in the composition in an amount effective for promoting the development of connective tissue in the body. The actual amount is not critical provided it is sufficient to promote such development. The daily dosage is preferably in the range of about 500 mg to about 3000 mg, more preferably in the range of about 1000 mg to about 2000 mg, and most preferably is about 1500 mg.

In a particularly preferred embodiment, the composition consists essentially of an effective amount of ferrous ion, an effective amount of an ascorbate and an effective amount of a glucosamine derivative. Especially preferred is a composition consisting essentially of an effective amount of ferrous sulphate, ferrous ascorbate or ferrous fumarate, an effective amount of ascorbic acid and an effective amount of glucosamine hydrochloride or glucosamine sulphate.

The dosage ranges described above are typically for humans. One skilled in the art can readily determine appropriate doses for other animals.

The compositions of the present invention may also include other factors that may be useful in treating a disease of connective tissue. These include glycosaminoglycans (GAGs) such as chondroitin.

Other minerals and vitamins which have other therapeutic indications may be present in the compositions. These include: zinc (in the form of zinc sulphate for example), potassium, sodium, calcium, magnesium, vitamin D and vitamin E.

The compositions are preferably formulated together with a pharmaceutically acceptable excipient or diluent. Such excipients or diluents as well as the methods of formulating the compositions are well known to those skilled in the art. Cellulose, maltodextrin and water are preferred.

In another particularly preferred embodiment, the composition consists essentially of an effective amount of ferrous ion, an effective amount of an ascorbate, an effective amount of a glucosamine derivative and a pharmaceutically acceptable excipient or diluent. Especially preferred is a composition consisting essentially of an effective amount of ferrous sulphate, ferrous ascorbate or ferrous fumarate, an effective amount of ascorbic acid, an effective amount of glucosamine hydrochloride or glucosamine sulphate, and water, cellulose or maltodextrin.

The compositions are generally formulated in a dosage form. Dosage forms include powders, tablets, capsules, solutions, suspensions, emulsions and other forms that are readily appreciated by one skilled in the art. The compositions may be administered orally, parenterally, intravenously or by any other convenient method. Capsules and tablets for oral administration are preferred.

The compositions of the present invention may also be admixed with a food or beverage and taken orally in such a manner. Foods or beverages may help mask the flavour of ferrous ion thus making the composition more palatable for consumption by humans or other animals. Fortified foods and beverages may be made by adding the composition of the present invention during the manufacturing of the food or beverage. Alternatively, the consumer may add the composition to the food or beverage near the time of consumption. Each ingredient of the composition may be added to the food or beverage together with the other ingredients or separately from the other ingredients. Examples of foods and beverages are cereals, snack bars, dairy products, fruit juices, powdered food and dry powder beverage mixes.

There is also provided a method for treating a disease of connective tissue, such as osteoarthritis, comprising administering a composition comprising an effective amount of ferrous ion and an effective amount of an ascorbate to a patient suffering from the disease. The method may further comprise administering the composition further including an effective amount of a glucosamine derivative.

In such methods, the patient preferably receives from about 0.5 mg to about 200 mg (more preferably from about 2 mg to about 200 mg) of ferrous ion per day and from about 40 mg to about 1000 mg of the ascorbate per day. More preferably, the patient receives from about 10 mg to about 18 mg of ferrous ion per day and from about 100 mg to about 1000 mg (or from about 40 mg to about 500 mg) of the ascorbate per day. When a glucosamine derivative is also administered, it is preferably administered in an amount from about 500 mg to about 3000 mg per day, more preferably in an amount from about 1000 mg to about 2000 mg per day.

One skilled in the art will understand that, in a method for treating diseases of connective tissue, daily dosage can be given all at once in a single dose or can be given incrementally in several smaller dosages. Thus, the compositions of the present invention can be formulated such that the recommended daily dose is achieved by the administration of a single dose or by the administration of several smaller doses.

It is apparent to one skilled in the art that the compositions of this invention can be included in a commercial package together with instructions for its use against a disease of connective tissue, such as osteoarthritis. Such a package may be in the form of a sachet, bottle or blisterpack but is not limited to such. Instructions are normally in the form of a written material but are not limited to such.

EXAMPLES

Example 1

Cell Culture Preparation

Cell cultures were prepared substantially as described in the prior art (S. Ekayanake and B. K. Hall, *Int. J. Dev. Biol.*, 38: 683–694 (1994)), the entire disclosure of which is hereby incorporated by reference. In general, cartilage precursor cells from the developing limb bud of normal chick embryos were isolated and a single cell suspension containing $2 \times 10^7$ cells/ml was prepared. For the production of micromass cultures, cells were plated as 10 μl drops on to bottoms of 24-well plastic tissue culture plates and incubated for 1 hour in a tissue incubator to allow cells to attach to the culture plate. Once cells are attached, cultures were flooded with liquid culture medium comprising:

a 3:1 mixture of Ham's F12 (from Gibco™) and BGJb (from Gibco™);

10% fetal bovine serum (from Gibco™);

about 75 μg/ml of ascorbic acid; and other normal ingredients known to those skilled in the art. This is the basic culture medium. Generally, the basic culture medium contains about 0.6 μg/ml ferrous sulphate due to its presence in the commercial medium. As can be appreciated from this example, the basic cell culture medium also contains about 75 μg/ml of ascorbic acid that was added during the cell culture preparation as described above. Cells were maintained in culture for up to 10 days. The culture medium that cells grew in was changed daily. Under these conditions, cartilage precursor cells produced cartilage tissue within 4 days, and the amount of cartilage present in cultures gradually increased with time.

Example 2

Effect of Ascorbic Acid on Cartilage Development

Figure 1:
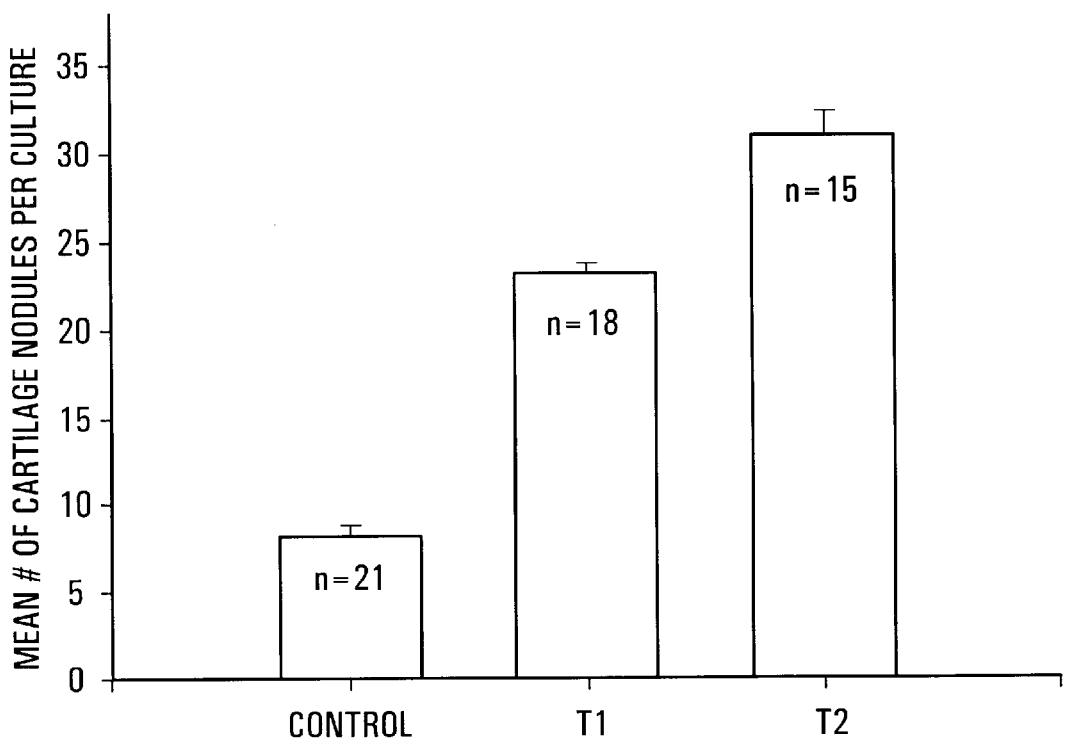
FIG. 1 is a graph showing the dose dependent effect of ascorbic acid on cartilage development.

Cultured cartilage cells were dosed with varying amounts of ascorbic acid. The amount of cartilage produced was quantified using standard procedures such as the number of cartilage nodules present per culture, the amount of cartilage matrix present per culture as measured by alcian blue spectrophotometry, and microphotography. FIG. 1 shows that ascorbic acid significantly enhances cartilage development in a dose-dependent manner. The Control bar in FIG. 1 represents the situation where no ascorbic acid was added during the cell culture preparation. It is thought that cartilage development in the Control experiment occurs because the cartilage cells themselves have a basal level of ascorbic acid in them. The $T_1$ bar represents the results obtained when the basic culture medium is used, that is, when 75 μg/ml of ascorbic acid is added during cell culture preparation as described in Example 1. The $T_2$ bar represents the results obtained when an additional 75 μg/ml of ascorbic acid is added to the basic culture medium to bring the total added ascorbic acid content to 150 μg/ml.

Example 3

Effect of Ferrous Sulphate on Cartilage Development

Figure 2:
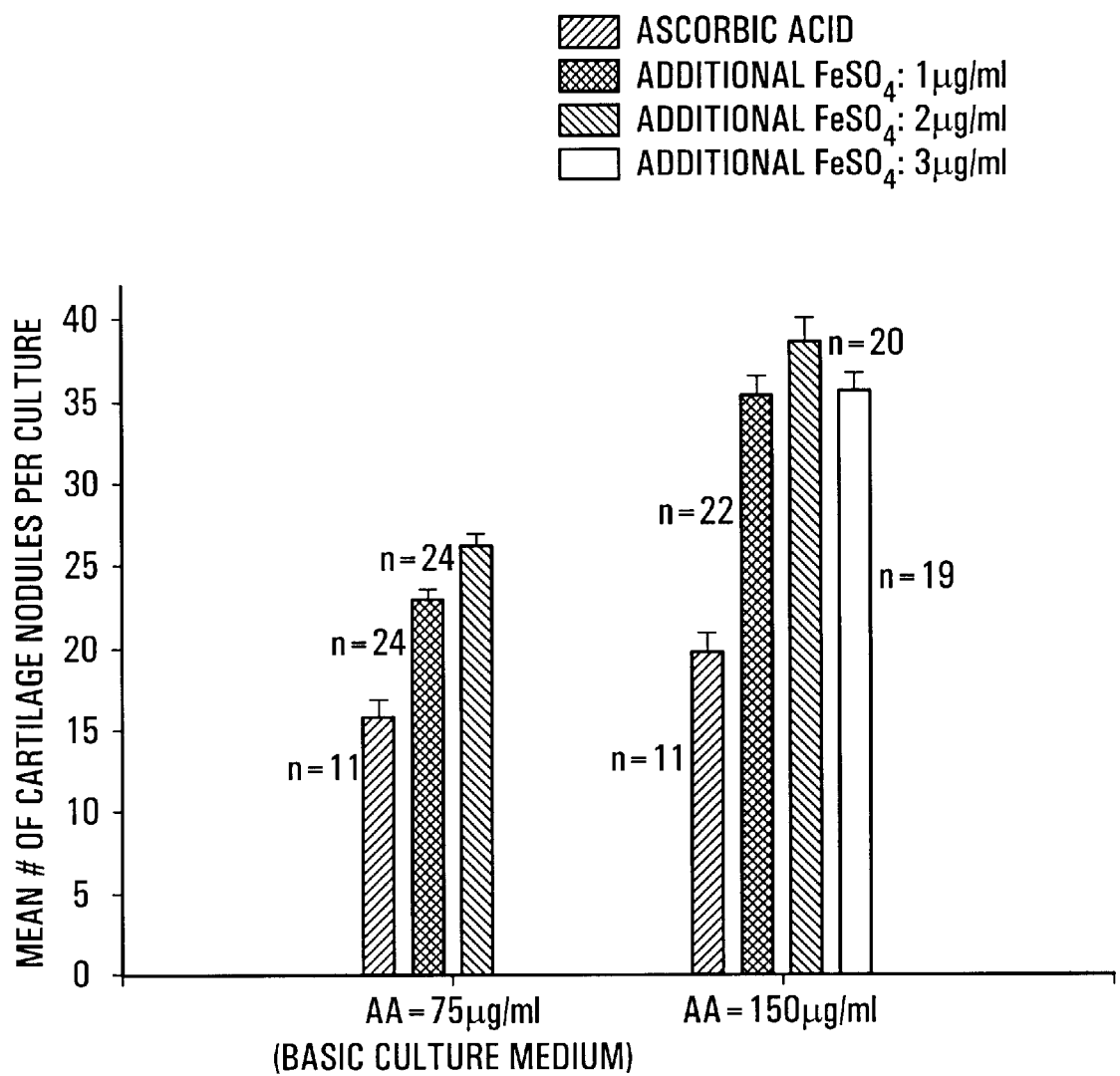
FIG. 2 is a graph showing the combined effect of ferrous sulphate (FeSO$_4$) and ascorbic acid (AA) on cartilage development and showing the individual effect of ferrous sulphate on cartilage development at a particular dose of ascorbic acid.

Cultured cartilage cells prepared as described in Example 1 were dosed with varying amounts of additional ferrous sulphate (test group) or no additional ferrous sulphate (control group). It is thought that the control group shows cartilage development due to the basal level of ferrous sulphate (about 0.6 μg/ml) and ascorbic acid (about 75 μg/ml) normally present in the basic culture medium. The amount of cartilage produced was quantified using standard procedures as outlined in Example 2. As shown in FIG. 2, the results indicate that, at a particular dose of ascorbic acid, ferrous sulphate significantly enhanced cartilage development in a dose-dependent manner.

Example 4

Synergistic Effect of Ferrous Sulphate and Ascorbic Acid on Cartilage Development Cultured cartilage cells were dosed with a combination of ferrous sulphate and ascorbic acid at different concentrations. As shown in FIG. 2, the results indicate that when the dose of ascorbic acid is increased, there is a greater than expected increase in cartilage development over the same dose range of ferrous sulphate. The results indicate that the combination of ferrous sulphate and ascorbic acid exert a synergistic effect on cartilage development and that the effect is dose dependent.

Example 5

Figure 3:
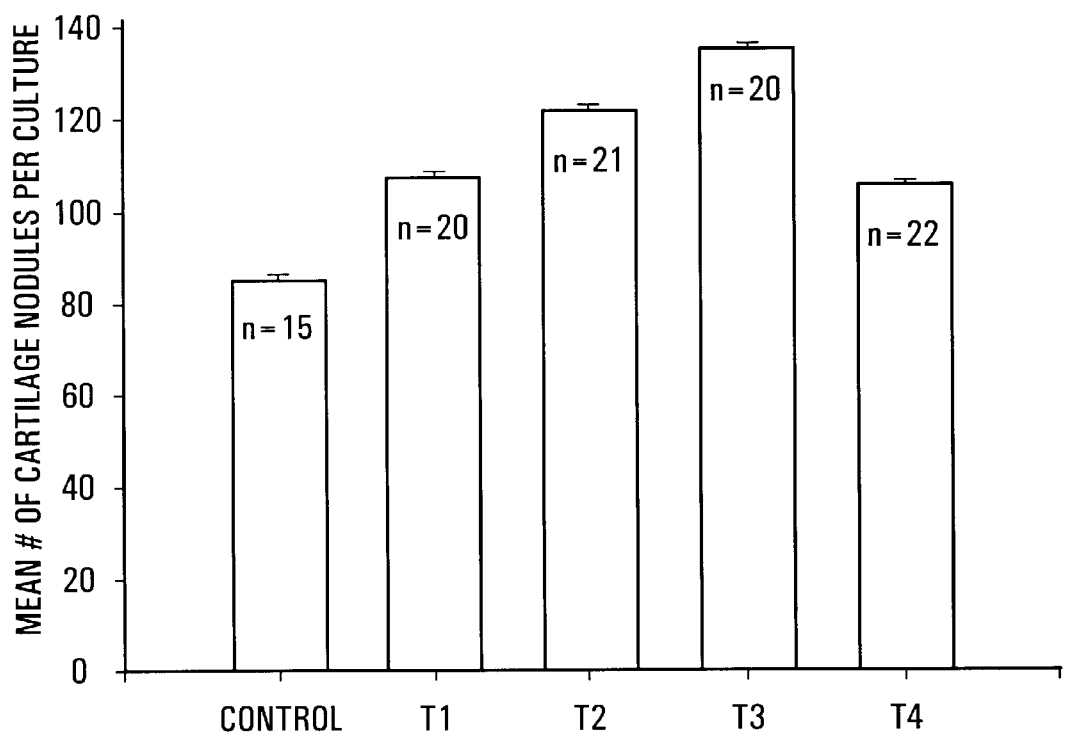
FIG. 3 is a graph showing the combined effect of ferrous sulphate (FeSO$_4$), ascorbic acid (AA) and glucosamine hydrochloride (GS—HCl) on cartilage development.

Effect of Ferrous Sulphate, Ascorbic Acid and Glucosamine Hydrochloride on Cartilage Development Cultured cartilage cells were dosed with varying concentrations of glucosamine hydrochloride in combination with optimal doses of ferrous sulphate and ascorbic acid. The amount of cartilage produced was quantified using standard procedures as outlined in Example 2. As shown in FIG. 3, cartilage development increased with increasing concentrations of glucosamine hydrochloride, with the greatest positive effect on cartilage development occurring at a concentration of glucosamine hydrochloride of 60 µg/ml. The amount of ferrous sulphate represented in FIG. 3 (2 µg/ml) is the amount of additional ferrous sulphate added and does not account for the basal level of ferrous sulphate present in the basic culture medium. The amount of ascorbic acid (150 µg/ml) represents the total amount of ascorbic acid including the 75 µg/ml normally added during the cell culture preparation as described in Example 1.

Example 6
Effect of Zinc Sulphate on Cartilage Development

Figure 4:
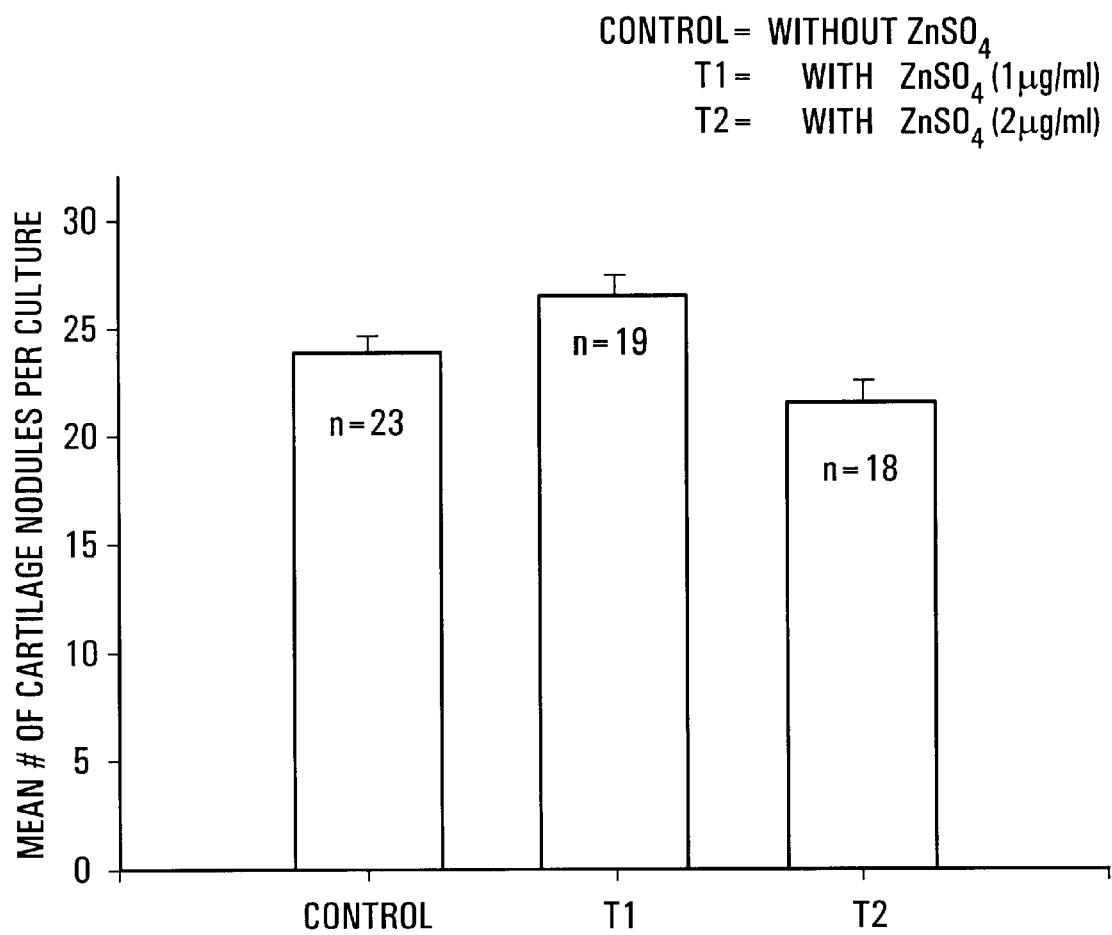
FIG. 4 is a graph showing the dose dependent effect of zinc sulphate (ZnSO$_4$) on cartilage development.

The effect of zinc sulphate on cartilage development was also tested. Cultured cartilage cells prepared as described in Example 1 were dosed with varying concentrations of zinc sulphate. The results are shown in FIG. 4. There was no statistically significant increase in cartilage development between the control group that contained no zinc sulphate and the test groups that contained varying amounts of zinc sulphate. Therefore, zinc sulphate does not have the same cartilage enhancing effect as ferrous sulphate.

Example 7
Effect of Other Metal Sulphates on Cartilage Development

Similar experiments to that of Example 6 were conducted using potassium sulphate, cobalt (II) sulphate or nickel (II) sulphate instead of zinc sulphate. No statistically significant increase in cartilage development was observed between the control group and the test groups containing any of the metal sulphates. However, cobalt (II) sulphate appeared to significantly reduce the amount of cartilage produced in a dose-dependent manner.

Example 8

Comparison of Various Metal Sulphates with Ferrous Sulphate on Cartilage Development The combined effect of ascorbic acid with various metal sulphates (potassium sulphate, cobalt (II) sulphate and nickel (II) sulphate) on cartilage enhancement was tested using the procedure described in Example 1. The dose of ascorbic acid used was 150 µg/ml, which, as can be seen from Example 4, is a very effective dose. The amount of ascorbic acid added to the cultures was kept constant (150 µg/ml). The concentration of each of the metal ions was also kept constant (13 µM) and is comparable to the concentration of ferrous ions in 2 µg/ml of $FeSO_4 \cdot 7H_2O$. The amount of cartilage produced in each culture was measured using alcian blue spectrophotometric methods. The results indicate that of all the metal sulphates tested, only ferrous sulphate significantly enhanced the cartilage production when combined with ascorbic acid.

Example 9
Comparison of Various Iron Salts

Similar experiment to that of Example 6 were conducted using ferrous ascorbate, ferrous fumarate and ferric sulphate (containing $Fe^{3+}$, an oxidized form of iron). Both ferrous ascorbate and ferrous fumarate significantly enhanced cartilage production indicating that, regardless of the form of the salt, ferrous ion ($Fe^{2+}$) is capable of exerting cartilage enhancing effects. In contrast, there was no statistically significant difference observed between the control cultures and the cultures treated with ferric sulphate indicating the ineffectiveness of ferric ion ($Fe^{3+}$) in enhancing cartilage development.

Example 10
Comparison of a Composition of the Present Invention with Glucosamine-based Products on the Market Two leading brands of glucosamine-based products (Osteo Bi-Flex™ and Schiff™ glucosamine) were tested in comparison to a composition according to the present invention using an in vitro cartilage cell culture system designed to study the ability of various compounds to rescue degrading cartilage. This cartilage degradation monitoring system is an expansion of the cell culture method described in Example 1.

In summary, cartilage cell cultures were established as described in Example 1 and treated with the active ingredient mixture present in each of the above three products purchased or prepared in cell culture grade. (The composition of the present invention that was used contained 2 µg/ml ferrous sulphate, 150 µg/ml ascorbic acid and 100 µg/ml glucosamine hydrochloride. The composition using the active ingredients from Schiff™ glucosamine contained 100 µg/ml of glucosamine hydrochloride, 33 µg/ml of glucosamine sulphate and 33 µg/ml of N-acetyl glucosamine. The composition using the active ingredients from Osteo Bi-Flex™ contained 100 µg/ml glucosamine hydrochloride, 100 µg/ml galactosamine and 100 µg/ml glucuronic acid. (Galactosamine and glucuronic acid are the building blocks of chondroitin, which is in the Osteo Bi-Flex™ product.)) At day 4 when cartilage precursor cells have produced cartilage tissue, cultures were fed with the same medium containing the active ingredients plus 1 µM retinoic acid (RA). Retinoic acid has been previously shown to experimentally induce degradation of cartilage in a manner similar to what is seen in osteoarthritis. Eighteen hours after retinoic acid treatment, cultures were examined microscopically to evaluate the degree of degradation that has occurred in the cartilage tissue of each of the treatment groups, microscopic images were recorded using a digital image analysis system and the actual amount of cartilage tissue present in each of the cultures was quantified using alcian blue spectrophotometric methods.

Figure 5:
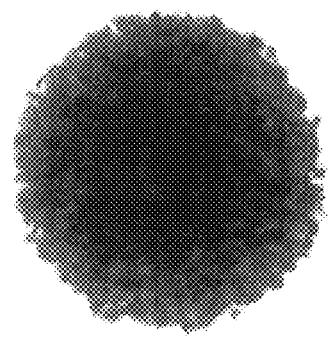
FIG. 5 depicts micrographs of cartilage cultures after treatment with a composition of the present invention and with prior art compositions.
Figure 5:
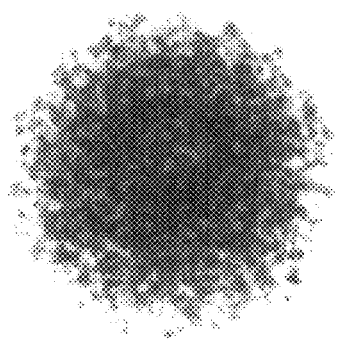
Figure 5:
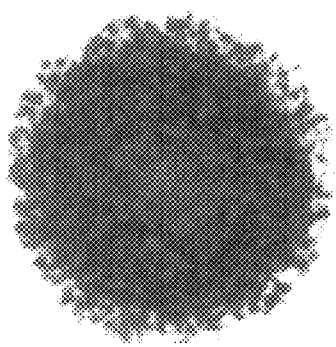
Figure 5:
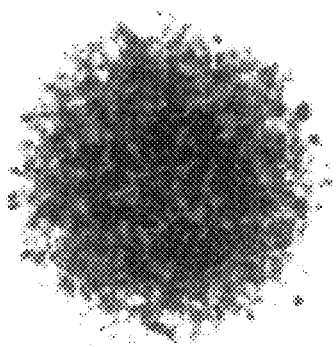
Figure 5:
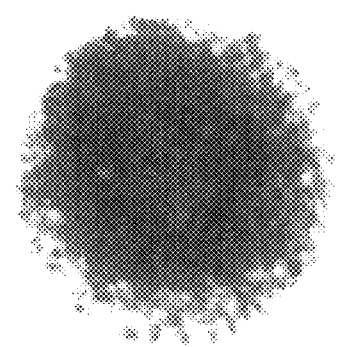

Microscopic images of a representative culture from each of the experimental groups are depicted in FIG. 5. These cultures have been stained with alcian blue to visualize cartilage tissue. The intensity of the blue stain corresponds to the amount of cartilage present. The experimental groups are as follows:

| | |
|---|---|
| Control | Not treated with RA or any of the test compositions |
| RA only | Treated with RA but not with any of the test compositions |
| RA + invention | Treated with RA and with a composition of the present invention |
| RA + Osteo Bi-Flex ™ | Treated with RA and with active ingredients in Osteo Bi-Flex ™ formulation |
| RA + Schiff ™ | Treated with RA and with active ingredients in Schiff ™ formulation |

Figure 6:
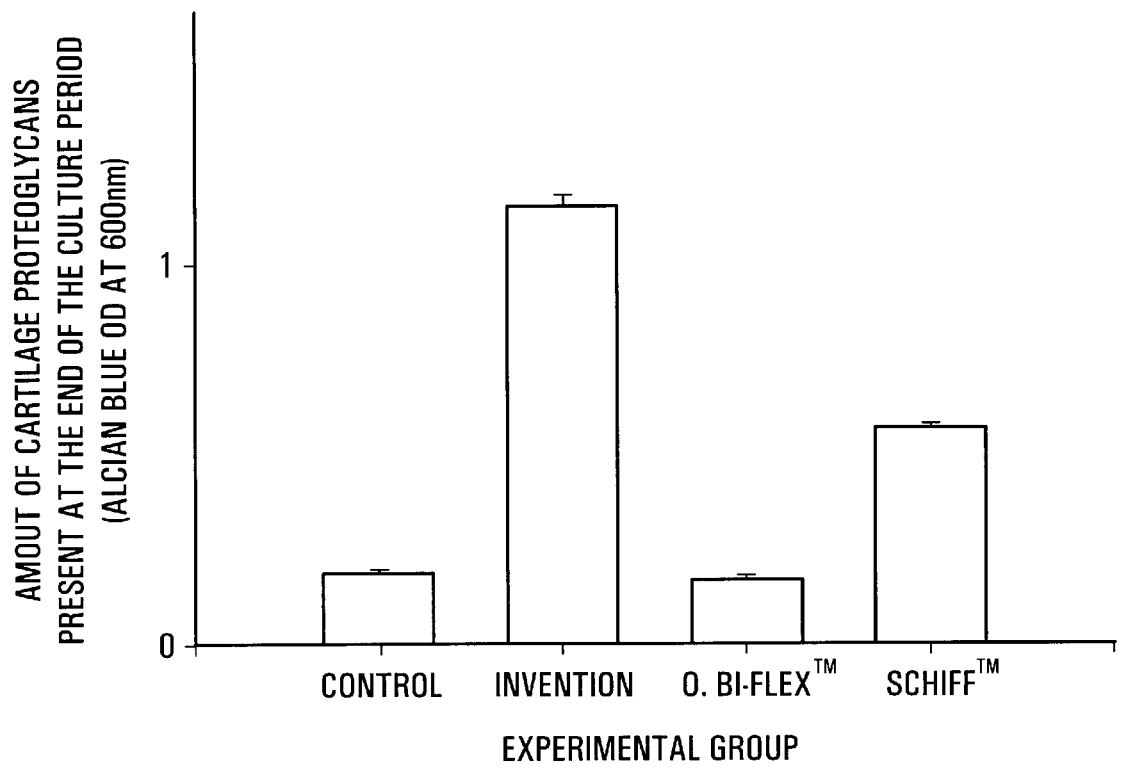
FIG. 6 is a graph comparing the effectiveness of a composition of the present invention to the effectiveness of prior art compositions.

The amount of cartilage present in each of the groups after the experimental induction of cartilage degradation is indicated in FIG. 6. FIG. 6 is a graph indicating the ability of each of the compositions to rescue degrading cartilage.

Both FIGS. 5 and 6 indicate that retinoic acid induces substantial degradation of cartilage as evidenced by the smaller amount of cartilage present in RA only treated cultures at the end of the culture period in comparison to the control cultures that were not treated with retinoic acid. However, even in the presence of RA, cultures fed with the medium containing the composition of the present invention maintained a higher level of cartilage production in comparison to RA only treated cultures and also in comparison to cultures treated with RA plus the active ingredients present in the other two prior art products. These results indicate the ability of compositions of the present invention to rescue degrading cartilage, which is a feature very important in treating the cause of osteoarthritis. These results also indicate the improved effectiveness of the compositions of the present invention in comparison to prior art formulations.

It is apparent to one skilled in the art that many variations on the present invention can be made without departing from the scope or spirit of the invention claimed herein.

What is claimed is:

1. A composition for treating osteoarthritis, the composition comprising:
   a therapeutically effective amount of ferrous ion;
   a therapeutically effective amount of an ascorbate; and
   a therapeutically effective amount of a glucosamine derivative.

2. The composition according to claim 1, wherein the ferrous ion is provided in the form of an acid salt.

3. The composition according to claim 1, wherein the ferrous ion is provided in the form of ferrous sulphate, ferrous fumarate or ferrous ascorbate.

4. The composition according to claim 1, wherein the ascorbate is provided in the form of ascorbic acid or a salt of ascorbic acid.

5. The composition according to claim 1, wherein the glucosamine derivative is glucosamine hydrochloride or glucosamine sulphate.

6. The composition according to claim 1, wherein:
   a) the ferrous ion is provided in the form of ferrous sulphate, ferrous fumarate or ferrous ascorbate;
   b) the ascorbate is provided in the form of ascorbic acid, calcium ascorbate or ferrous ascorbate; and,
   c) the glucosamine derivative is glucosamine hydrochloride or glucosamine sulphate.

7. The composition according to claim 1, further comprising a pharmaceutically acceptable excipient or diluent.

8. The composition claim 6, further according to further comprising a pharmaceutically acceptable excipient or diluent.

9. The composition according to claim 8 formulated as a powder, tablet, capsule, solution, suspension or emulsion.

10. The composition according to claim 1 in admixture with a food or beverage.

11. The composition according to claim 6 admixture with a food or beverage.

12. A method for treating osteoarthritis comprising administering to a patient suffering from osteoarthritis, a composition comprising a therapeutically effective amount of ferrous ion and a therapeutically effective amount of an ascorbate.

13. The method according to claim 12 wherein the patient is human, a dog, a cat, a pig, a horse, a cow, a goat or a sheep.

14. The method according to claim 12, wherein the patient is human and receives from about 0.5 mg to about 200 mg of the ferrous ion per day and from about 40 mg to about 1000 mg of the ascorbate per day.

15. The method according to claim 12, wherein the patient is human and receives from about 10 mg to about 18 mg of the ferrous ion per day and from about 100 mg to about 1000 mg of the ascorbate per day.

16. The method according to claim 12, wherein the patient is human and receives from about 10 mg to about 18 mg of the ferrous ion per day and from about 40 mg to about 500 mg of the ascorbate per day.

17. The method according to claim 12, wherein the composition further comprises a therapeutically effective amount of a glucosamine derivative.

18. The method according to claim 17, wherein the patient receives from about 500 mg to about 3000 mg of the glucosamine derivative per day.

19. The method according to claim 18, wherein the patient receives from about 1000 to about 2000 mg of the glucosamine derivative per day.

20. The method according to claim 17, wherein the ferrous ion is provided in the form of ferrous sulphate, ferrous fumarate or ferrous ascorbate, the ascorbate is provided in the form of ascorbic acid, calcium ascorbate or ferrous ascorbate, and the glucosamine derivative is provided in the form of glucosamine hydrochloride or glucosamine sulphate.

21. The method according to claim 20, wherein the composition further comprises a pharmaceutically acceptable excipient or diluent.

22. The method according to claim 21, wherein the composition is administered in the form of a powder, tablet, capsule, solution, suspension or emulsion.

23. A kit comprising:
   a composition comprising a therapeutically effective amount of ferrous ion a therapeutically effective amount of an ascorbate, and a therapeutically effective amount of a glucosamine derivative; and
   instructions for use of said composition for treating osteoarthritis in a subject.

24. The kit according to claim 23, the ferrous ion is provided the form of an acid salt.

25. The kit according to claim 23, wherein the ferrous ion is provided in the form of ferrous sulphate, ferrous fumarate or ferrous ascorbate.

26. The kit according to claim 23, wherein the ascorbate is provided in the form of ascorbic acid or a salt of ascorbic acid.

27. The kit according to claim 23, wherein the glucosamine derivative is glucosamine hydrochloride or glucosamine sulphate.

28. The kit according to claim 27, wherein the ferrous ion is provided in the form of ferrous sulphate, ferrous fumarate or ferrous ascorbate; and wherein the ascorbate is provided in the form of ascorbic acid or a salt of ascorbic acid.

* * * * *